United States Patent
Ding et al.

(10) Patent No.: US 9,586,197 B2
(45) Date of Patent: *Mar. 7, 2017

(54) SOLID HETEROGENEOUS CATALYST FOR OLEFIN HYDROFORMYLATION REACTION AND PRODUCTION METHOD AND USE THEREOF

(71) Applicant: DALIAN INSTITUTE OF CHEMICAL PHYSICS, CHINESE ACADEMY OF SCIENCES, Dalian (CN)

(72) Inventors: Yunjie Ding, Dalian (CN); Miao Jiang, Dalian (CN); Li Yan, Dalian (CN); Ronghe Lin, Dalian (CN)

(73) Assignee: DALIAN INSTITUTE OF CHEMICAL PHYSICS, CHINESE ACADEMY OF SCIENCES, Dalian (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/102,287

(22) PCT Filed: Dec. 11, 2013

(86) PCT No.: PCT/CN2013/089054
§ 371 (c)(1),
(2) Date: Jun. 7, 2016

(87) PCT Pub. No.: WO2015/085506
PCT Pub. Date: Jun. 18, 2015

(65) Prior Publication Data
US 2016/0318009 A1   Nov. 3, 2016

(51) Int. Cl.
*C07C 45/50* (2006.01)
*B01J 31/00* (2006.01)
*B01J 31/24* (2006.01)
*B01J 35/10* (2006.01)
*B01J 37/04* (2006.01)
*B01J 37/08* (2006.01)
*C08J 9/28* (2006.01)

(52) U.S. Cl.
CPC ............. *B01J 31/24* (2013.01); *B01J 31/00* (2013.01); *B01J 35/108* (2013.01); *B01J 35/1019* (2013.01); *B01J 35/1023* (2013.01); *B01J 35/1028* (2013.01); *B01J 35/1038* (2013.01); *B01J 35/1042* (2013.01); *B01J 35/1047* (2013.01); *B01J 37/04* (2013.01); *B01J 37/08* (2013.01); *C07C 45/50* (2013.01); *C07C 45/505* (2013.01); *C08J 9/286* (2013.01); *B01J 2231/321* (2013.01); *B01J 2531/822* (2013.01); *B01J 2531/845* (2013.01); *C08J 2201/05* (2013.01); *C08J 2205/042* (2013.01); *C08J 2205/044* (2013.01); *C08J 2207/00* (2013.01); *C08J 2343/02* (2013.01)

(58) Field of Classification Search
CPC .. C07C 45/50; B01J 31/29; B01J 35/00; B01J 37/04; B01J 37/08
USPC ......................................................... 568/454
See application file for complete search history.

(56) References Cited

U.S. PATENT DOCUMENTS 4,252,678 A    2/1981 Smith

FOREIGN PATENT DOCUMENTS

CN          1043640 A      7/1990
CN        102281948 A     12/2011

OTHER PUBLICATIONS

Kausik Mukhopadhyay et al (Chem Mater, 2003, 15:1766-1777).
Bassam El Ali et al (Journal of Molecular Catalysis A: Chemical, 2006, 250:153-162).
N. Sudheesh et al (Journal of Molecular Catalysis A: Chemical, 2008, 296:61-70).
N. Sudheesh et al (Applied Catalysis A: General, 2012, 415-416:124-131).
Ki-Chang Song et al (Catalysis Today, 2011, 164:561-565).
Ranh Nguyen Thi Ha et al (Catalysis Communications, 2012, 25:136-141).
Balue et al (J. Mol. Catal. A: Chem., 1999, 137: 193-203).
Zeelie et al (Appl. Catal. A: Gen, 2005, 285: 96-109).
Ricken et al (J. Mol. Catal. A: Chem, 2006, 257: 78-88).
Li et al., "Study on the Suzuki Coupling Reaction Catalyzed by Palladium Catalyst supported in Microcapsule Film" CMFD, No. 8 (2008) (English Abstract is included).

*Primary Examiner* — Sikarl Witherspoon
(74) *Attorney, Agent, or Firm* — Enshan Hong; VLP Law Group LLP

(57) ABSTRACT

A solid heterogeneous catalyst consisting of a metal component and an organic ligand polymer, wherein the metal component is one or more of Rh, Ir or Co, the organic ligand polymer is a polymer having a large specific surface area and hierarchical porosity formed by polymerizing an organic ligand monomer containing P and alkenyl group and optional N via a solvothermal polymerization process, the metal component forms coordinated bond with the P atom or N in backbone of the organic ligand polymer and exists in a monoatomic dispersion state; when the catalyst is used in an olefin hydroformylation reaction, the metal component and the P and/or N atom form in situ an intermediate active species similar to homogeneous catalyst due to the coordination effect, and the catalyst has an excellent catalytic property, can be easily separated, and has a relatively high stability.

9 Claims, 1 Drawing Sheet

SOLID HETEROGENEOUS CATALYST FOR OLEFIN HYDROFORMYLATION REACTION AND PRODUCTION METHOD AND USE THEREOF

RELATED APPLICATIONS

This is a U.S. national stage of international application No. PCT/CN2013/089054 filed on Dec. 11, 2013.

FIELD OF THE INVENTION

The invention relates to a solid heterogeneous catalyst for olefin hydroformylation reaction, and a production method and use thereof, which belongs to the field of heterogeneous catalytic techniques.

BACKGROUND

Olefin hydroformylation is one of the important methods for synthesizing aldehydes and alcohols, and the like industrially. Currently, over 10 million tons of aldehydes and alcohols are produced by the olefin hydroformylation technique annually in the world. This reaction can produce aldehydes from olefins under less severe conditions, and further, the product aldehydes can be converted to alcohols by hydrogenation. Homogeneous catalytic systems exhibit a relatively high catalytic activity and a target product selectivity under relatively mild reaction conditions, but the separation of the catalyst from the reaction materials is difficult. As compared with homogeneous catalysis, the most important advantage of heterogeneous catalysis is that it is easy to separate the catalyst from the reaction materials, with the main problems of severe reaction conditions, a relatively low reactivity, and the like. At present, the main research hotspot of hydroformylation focuses on developing a novel heterogenized catalyst so that it not only has the advantage of heterogeneous catalysis, being easy to separate the catalyst from the reaction materials, but also exhibits a high reactivity and mild reaction conditions of homogeneous catalysis.

Kausik Mukhopadhyay et al (Chem Mater, 2003, 15:1766-1777) performed passivation treatment to the outer surface of the molecular sieves MCM-41 and MCM-48 with diphenyldichlorosilane, and then modified the inner surface of the molecular sieves with 3-aminopropyltrimethoxysilane, so that $HRh(CO)(PPh_3)_3$ can be selectively immobilized on the inner surface of the molecular sieves. The most notable highlight is that the authors selectively immobilized $HRh(CO)(PPh_3)_3$ on the inner surface of the molecular sieves MCM-41 and MCM-48 inventively. However, this heterogeneous catalytic system has a relatively low reactivity in view of the reaction effect of catalyst, and the results of recycle show that the recyclability of the catalyst is relatively poor and the loss of metal is relatively serious.

Bassam El Ali et al (Journal of Molecular Catalysis A: Chemical, 2006, 250:153-162) immobilized a heteropolyacid on a MCM-41 support, while immobilizing $HRh(CO)(PPh_3)_3$ on the MCM-41 support. The research showed that the presence of the heteropolyacid can not only improve the reactivity of hydroformylation, but also effectively reduce the problem of metal loss, so as to ensure the stability of the reaction of the heterogeneous catalyst.

N. Sudheesh et al (Journal of Molecular Catalysis A: Chemical, 2008, 296:61-70) encapsulated the $HRh(CO)(PPh_3)_3$ catalyst in situ in the HMS mesoporous molecular sieve, and applied it to hydroformylation reactions of long chain olefins. The authors took the reaction of 1-hexene in slurry bed as the focal point of research, and discussed the effects of the temperature, the partial pressure of carbon monoxide, the partial pressure of hydrogen, the amount of catalyst, and the like, on the reactivity, and the results of recycle of catalyst show that the catalyst has a relatively good recyclability. Thereafter, N. Sudheesh et at (Applied Catalysis A: General, 2012, 415-416:124-131) applied the catalytic system to the hydroformylation reaction of propylene, in which $HRh(CO)(PPh_3)_3$ is encapsulated in situ in the HMS mesoporous molecular sieve. As a nanoscale reactor, the HMS mesoporous molecular sieve exhibits a relatively high stability in research of recycle. However, there is still a relatively large difference in reactivity, as compared with homogeneous catalytic systems.

Ki-Chang Song et at (Catalysis Today, 2011, 164:561-565) subjected SBA-15 to post-modification by two methods. One method is a passivation treatment to the outer surface of SBA-15 with diphenyldiethoxysilane, and then modification to the inner surface of SBA-15 with N-(2-aminoethyl)-3-aminopropylmethyldimethoxysilane, so as to achieve the purpose of immobilizing $Rh_4(CO)_{12}$ to SBA-15 by reacting $Rh_4(CO)_{12}$ with the amino group in the modified inner surface. The other method is modification to the surfaces of SBA-15 with N-(2-aminoethyl)-3-aminopropylmethyldimethoxysilane directly, so as to achieve the purpose of immobilizing $Rh_4(CO)_{12}$ to SBA-15 by reacting $Rh_4(CO)_{12}$ with the amino group in the modified outer/inner surface of the molecular sieve. The research shows that the immobilized catalyst formed by the second treatment method exhibits more excellent activity and stability in hydroformylation reactions. The authors explained the reason why the catalyst has a better activity lies in the simultaneous modification to the inner and outer surfaces, which can allow $Rh_4(CO)_{12}$ to be dispersed more uniformly in the inner and outer surfaces of the molecular, so that the homogeneous catalyst has a larger free space. The authors' research shows that the normal/isomeric ratio (n/i) is relatively high because of the steric hindrance effect of the ligand, which facilitates the generation of linear aldehydes.

Hanh Nguyen Thi Ha et at (Catalysis Communications, 2012, 25:136-141) produced a supported ionic liquid heterogeneous catalyst from $Rh(acac)(CO)_2$ and a ligand TPPTS, and applied it to the hydroformylation reaction of ethylene. The authors researched the effects of the amount of the ionic liquid, the reaction temperature, the pressure, and the like, on the catalytic activity. The research shows that a high amount of the ionic liquid is disadvantageous for the reactivity of hydroformylation. The Characterizations performed by FTIR, SEM, and EDX analysis, and the like, indicate that the reason for the deactivation under a relatively high amount of the ionic liquid is that the ionic liquid overflows from the pores of the support, resulting in the loss of the homogeneous catalyst, and thus the notable decrease of the reactivity.

The researches mentioned above are classified into two methods. One method is pre-modification to the support to make the support have a corresponding organic functional group, and then immobilization of the homogeneous catalyst on the support by the chemical reaction between the catalyst, such as homogeneous $HRh(CO)(PPh_3)_3$, and the organic functional group. The other method is in situ addition of the catalyst, such as homogeneous $HRh(CO)(PPh_3)_3$, during the synthesis of the support, enabling the interaction between the homogeneous catalyst and the organic functional group, so that the homogenous catalyst is formed in the support, while the support is synthesized. The general concept of the two methods mentioned above is the reaction of an organic functional group with a homogeneous catalyst, so as to immobilize the homogeneous catalyst on a heterogeneous support. The significant problems in these two methods are the loss of the homogeneous catalyst, and the decrease of the reactivity of the homogeneous catalyst when being immobilized on the support. These two problems are the primary bottlenecks which restrict the homogeneous immobilization for hydroformylation.

Balue et at (J. Mol. Catal. A: Chem., 1999, 137: 193-203) used a cation exchange resin as the support, and prepared a heterogeneous catalyst by immobilizing a rhodium-sulfur compound. However, the heterogeneous catalyst exhibits poor stability and relatively serious Rh loss phenomenon, as shown by the recycle experiment of styrene hydroformylation. Zeelie et at (Appl. Catal. A: Gen, 2005, 285: 96-109) modified polyethylene fibers with styrene and p-styrenediphenylphosphine, then anchored $Rh(acac)(CO)_2$ onto the modified polyethylene fibers, and the results of ethylene hydroformylation show that the catalyst provides a relatively high conversion but a poor stability at 100° C. and 5 bar, and that after 50 h, the reactivity rapidly decreases and the deactivation phenomenon of the catalyst is relatively serious. Ricken et at (J. Mol. Catal. A: Chem, 2006, 257: 78-88) modified the ligand NIXANTPHOS by various functionalization, and co-supported the modified ligand and Rh(acac) $(CO)_2$ on polyglycerol compound, and the results of 1-octene hydroformylation show that the catalyst provides a conversion up to about 90% at 80° C. and 20 bar. However, the industrial application of this catalyst is greatly limited, because the polymeric supports purchased commercially or produced by normal radical polymerization of styrene show the following problems: the formation of gel, swelling of the polymer, limited loading amount of the phosphorus ligand in the framework of the polymer, loss of the component having catalytic activity, and the like.

U.S. Pat. No. 4,252,678 discloses the production of a colloidal dispersion containing a transition metal, such as Rh, etc, in which the catalyst system is consisted of a transition metal component in form of a colloidal dispersion of 1.0 to 20.0 nm and (styrene/butadiene) functionalized copolymer terminated with a hydroxy group, and is used in the hydroformylation reaction of 1-octene. The catalyst prepared by this method cannot be used in fixed bed reactors and trickle bed reactors, and it is difficult to separate the catalyst from the product.

CN 102281948 A reports a polymer-supported transition metal catalyst complex and method for use, and produces a soluble polymer-supported rhodium catalyst having a narrow molecular weight distribution. However, all the processes for production of the catalyst, the catalytic reaction, and the separation of the catalyst are complicated. In the production of the catalyst, it is required to synthesize a soluble polymer by controlling functional monomers and styrene, etc., and then introduce a ligand, and at last support the Rh catalyst. It is required to add compressed gas during the catalytic reaction. The catalyst is separated from the reaction mixture by means of nanofiltration, and the reaction results are not ideal, either.

The paper "*Study on the Suzuki Coupling Reaction Catalyzed by Palladium Catalyst supported in Microcapsule Film*" (Kaixiao LI, CMFD, No. 8) reports that a Pd-based catalyst is produced by using a microcapsule material as the support, which is connected with a phosphorus ligand in the polystyrene microcapsule film, and used in Suzuki coupling reaction. However, the microcapsule material is a copolymer material, rather than a monopolymer material. The dispersion state of the transition metal component in this catalyst is not mentioned.

SUMMARY OF THE INVENTION

In order to solve the problems mentioned above, the object of the invention is to provide a novel solid heterogeneous catalyst, in which the metal component is supported by the organic ligand polymer itself, and the production method and use thereof.

For this purpose, the invention provides a solid heterogeneous catalyst for olefin hydroformylation reaction, wherein the solid heterogeneous catalyst consists of a metal component and an organic ligand polymer, wherein the metal component is one or more of Rh, Ir or Co, the organic ligand polymer is a polymer having a large specific surface area and hierarchical porosity formed by polymerizing an organic ligand monomer containing P and alkenyl group and optional N via a solvothermal polymerization process, the metal component forms coordinated bonds with the P atom or N in the backbone of the organic ligand polymer and exists in a monoatomic dispersion state.

In a preferred embodiment, the metal component accounts for 0.005 to 5.0% based on the total weight of the solid heterogeneous catalyst.

In a preferred embodiment, the organic ligand monomer is an organic phosphine ligand monomer containing P and vinyl aromatic hydrocarbon and optional N.

In a preferred embodiment, the organic ligand polymer has a specific surface area of 100 to 3000 $m^2/g$, a pore volume of 0.1 to 5.0 $cm^3/g$, and a pore size distribution of 0.2 to 50.0 nm.

The invention also provides a method for producing the solid heterogeneous catalyst mentioned above, comprising:

a) adding a radical initiator into an organic solvent containing an organic ligand monomer in an autoclave for synthesis at 273 to 473 K and under the protection of inert gas, and stirring it for 0.5 to 100 h;

b) keeping the solution of step a) in an autoclave for synthesis for 0.5 to 100 h at 273 to 473 K and under the protection of inert gas, to perform a solvothermal polymerization reaction;

c) drawing off the solvent under vacuum at room temperature after the completion of step b), thereby obtaining the organic ligand polymer;

d) placing the organic ligand polymer in an organic solvent containing an active metal component, stirring it at 273 to 473 K and under the protection of inert gas for 0.5 to 100 h, and then drawing off the solvent under vacuum at room temperature, thereby obtaining the solid heterogeneous catalyst, in which the metal component is supported by the organic ligand polymer itself.

In a preferred embodiment, the organic solvent used in steps a) and d) is one or more of benzene, toluene, tetrahydrofuran, methanol, ethanol, or trichloromethane; the radical initiator used in step a) is one or more of cyclohexanone peroxide, dibenzoyl peroxide, tert-butyl hydroperoxide, azodiisobutyronitrile, or azodiisoheptanitrile.

In a preferred embodiment, the organic ligand monomer is an organic phosphine ligand monomer containing vinyl, and the organic solvent is benzene, toluene, or tetrahydrofuran.

In a preferred embodiment, the weight ratio of the radical initiator to the organic ligand monomer is 1:500 to 1:5.

The invention also provides use of the solid heterogeneous catalyst mentioned above in an olefin hydroformylation reaction, wherein the olefin hydroformylation reaction is carried out with olefins and CO/$H_2$ mixed gas in presence of the solid heterogeneous catalyst in a fixed bed, a trickle bed, a slurry bed or an autoclave reactor, wherein the reaction temperature is 323 to 573K, the reaction pressure is 0.1 to 20.0 MPa, and the volume space velocity of the gas is 100 to 20000 $h^{-1}$.

The advantageous effects of the invention include, but not limited to the following aspects:

As compared with the existing hydroformylation catalysts, for the solid heterogeneous catalyst of the invention, the production method of the catalyst is simple. Since the organic ligand polymer, which contains phosphorus (P) and optional nitrogen (N) and has a large specific surface area and hierarchical porosity, acts as both of a ligand and a support, the active metal component in the catalyst self-supported a metal component exists in a monoatomic dispersion state. Such a catalyst exhibits a high hydroformylation reactivity and good selectivity for aldehyde products. In particular, since the micropores in the hierarchical porosity has the function of configuration-selective catalysis, the selectivity and yield of normal aldehydes in the hydroformylation reactions of high carbon olefins are greatly increased. The metal component forms chemical coordinated bonds with P and/or N in the organic ligand polymer, and still remains the dispersion state of single metal atoms in a catalyst after running a long time, so it exhibits a very high stability, and the loss of metal component and/or ligand is not observed. A catalyst of the invention is a heterogeneous catalyst macroscopically, so it has notable advantages in recovery, recycle, and separation of reactants and products, and thus has a broad industrial prospect.

DETAILED DESCRIPTION OF EMBODIMENTS

Figure 1:
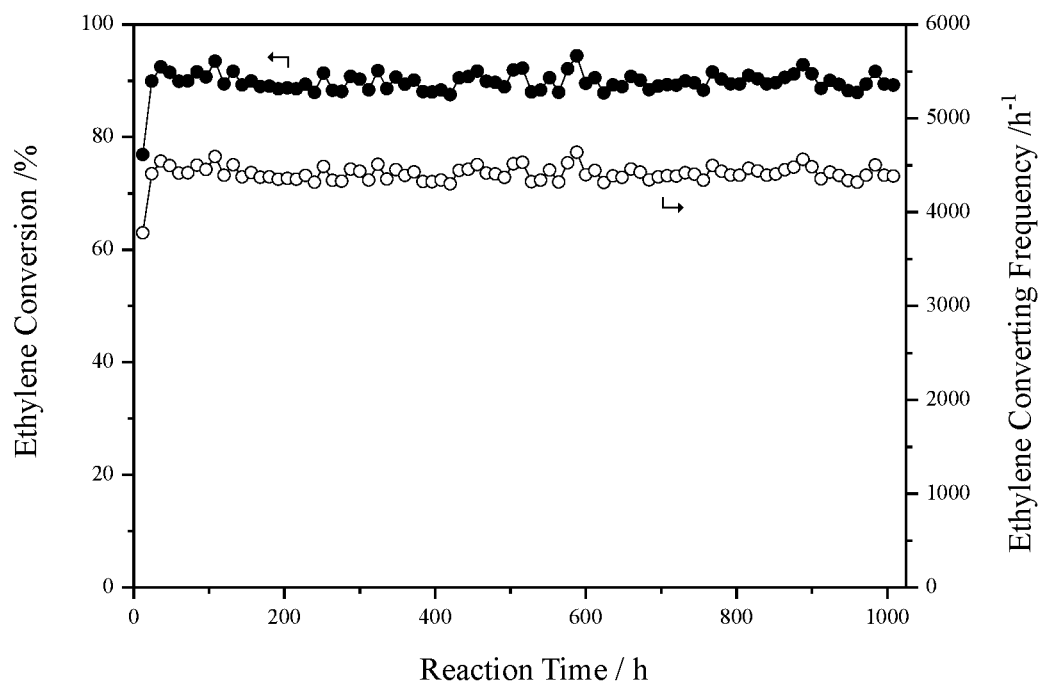
FIG. 1 shows the result of the reaction stability of a catalyst of the invention in ethylene hydroformylation after more than 1000 h.

On the basis of research of various homogeneous immobilization methods, the invention forms an organic ligand polymer having a large specific surface area and hierarchical porosity by polymerization in an autoclave, in which an organic phosphine ligand having alkenyl group (e.g. vinyl) introduced by the aromatic ring is used as the monomer for the polymerization and the solvothermal polymerization synthesis process is used, and new sites having catalytic activity is formed by the function of coordinated bonds between P and/or N atom having lone pair electrons and the empty orbital of the active transition metal ion, wherein a large amount of the P and/or N atoms are exposed out of the organic ligand polymer present in the backbone of the polymer. Herein, such a catalyst is referred to as a catalyst in which the active metal component is supported by the organic ligand polymer itself. On one hand, the organic ligand polymer acts as the ligand for the active metal component, and on the other hand, it acts as a support having a high specific surface area for supporting a highly dispersed active metal component. It is shown by research through modern characterization technologies, such as EXAFS, $^{31}$P NMR, HRTEM, FT-IR, and the like, that in this kind of catalysts in which the metal is supported by the organic ligand polymer itself, the active metal component exists in a monoatomic dispersion state, and the metal ion forms chemical bonds with P and/or N in the organic ligand polymer, and further, the metal in the catalyst, which has run for a long time, still remains in the monoatomic dispersion state, which means that the active site of homogeneous catalysis plays a role in the olefin hydroformylation reaction, and can exist in the organic ligand polymer stably, so that the chemical coordinated bonds formed of the metal component with the P and/or N in the organic ligand polymer solves the problem that the ions of active atoms intend to be lost. Thus, it enables the catalyst of the invention in which the active metal component is supported by the organic ligand polymer itself to solve the problems present in the immobilization of homogeneous catalysis so far, such as the decrease of reactivity, loss of active components, and the like. That is to say, it has a prospect in solving the problem of poor reaction stability.

More specifically, the solid heterogeneous catalyst provided by the invention consists of an organic ligand polymer and an active metal component supported by the organic ligand polymer itself, wherein the metal component is one or more of Rh, Ir or Co, the organic ligand polymer is a polymer having a large specific surface area and hierarchical porosity formed by a polymerization reaction, in which an organic ligand monomer containing P and alkenyl group and optional N is subjected to a solvothermal polymerization process in an autoclave, and the metal component forms coordinated bonds with the P atom or N in the backbone of the organic ligand polymer and exists in a monoatomic dispersion state. The organic ligand monomer is preferably an organic phosphine ligand monomer containing P and vinyl aromatic hydrocarbon and optional N. Additionally or preferably, the metal component accounts for 0.005 to 5.0 wt. % based on the total weight of the catalyst, and more preferably, the metal component accounts for 0.01 to 5.0 wt. % based on the total weight of the catalyst Preferably, in the catalyst mentioned above, the organic ligand polymer has a specific surface area of 200 to 2000 $m^2$/g, a pore volume of 0.5 to 5.0 $cm^3$/g, and a pore size distribution of 0.5 to 50.0 nm.

The catalyst provided by the invention, in which a metal is supported by an organic ligand polymer itself, can be produced by the following method, for example:

a) adding a radical initiator into an organic solvent containing an above-mentioned organic ligand monomer (such as a vinyl-functionalizing triphenylphosphine ligand, or a vinyl-functionalizing diphenylpyridylphosphine ligand) in an autoclave for synthesis at 273 to 473 K and under the protection of inert gas (such as nitrogen or argon), and stirring it for 0.5 to 100 h. Here, preferably, the solvent may be one or more of benzene, toluene, tetrahydrofuran, methanol, ethanol, or trichloromethane, the radical initiator may be one or more of cyclohexanone peroxide, dibenzoyl peroxide, tert-butyl hydroperoxide, azodiisobutyronitrile, or azodiisoheptonitrile. Preferably, the weight ratio of the radical initiator to the organic ligand monomer is 1:500 to 1:5.

b) keeping the above-mentioned solution in an autoclave for synthesis for 0.5 to 100 h at 273 to 473 K and under the protection of inert gas, to perform a solvothermal polymerization reaction by using a solvothermal polymerization method;

c) drawing off the solvent under vacuum at room temperature from the solution after polymerization mentioned above, so as to obtain an organic phosphine polymer support containing P and vinyl group and optional N and having a large specific surface area and hierarchical porosity;

d) placing the organic phosphine polymer support into an organic solvent (which may be the same solvent as that in the above step a)) containing a metal component, stirring it at 273 to 473 K and under the protection of inert gas (such as nitrogen or argon) for 0.5 to 100 h, cooling it down to the room temperature after the stirring, and drawing off the solvent under vacuum at room temperature, so as to obtain a solid heterogeneous catalyst consisting of the organic ligand polymer and an active metal component supported by the organic ligand polymer itself.

The catalyst can be used for catalyzing olefin hydroformylation reactions, which can be carried out in a fixed bed or a trickle bed, a slurry bed or an autoclave reactor. The typical operation conditions of the reactions are as follows: the reaction temperature of 323 to 573 K, the reaction pressure of 0.5 to 20.0 MPa, and the space velocity of the gas of 100~20000 $h^{-1}$. After evaluating the catalyst in the reaction, the results show that the solid heterogeneous catalyst of the invention, which consists of the organic ligand polymer and an active metal component supported by the organic ligand polymer itself, has an excellent catalytic activity, selectivity and stability. Furthermore, the catalyst can be separated from the products easily and recycled.

In production of the catalyst of the invention, the organic ligand monomer used can include, but not limited to, one or more of the followings:

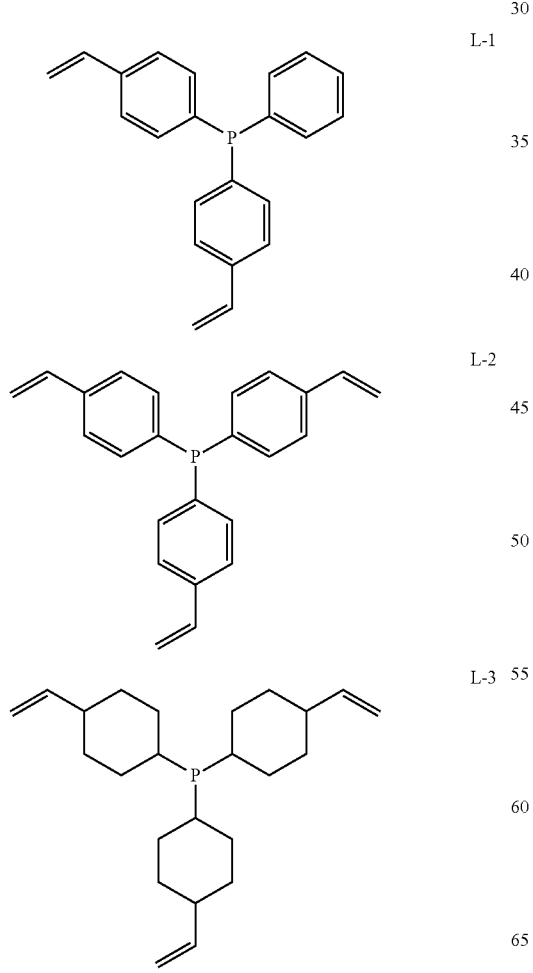

-continued

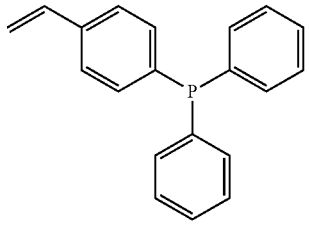
L-4

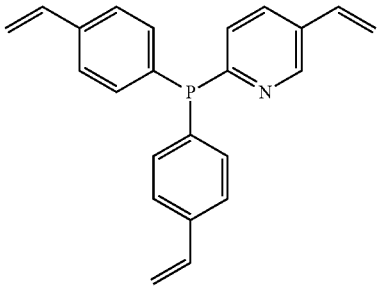
L-5

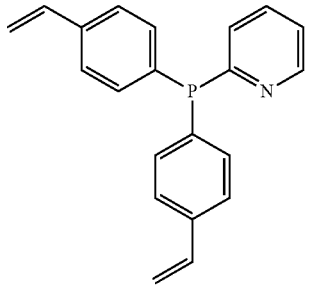
L-6

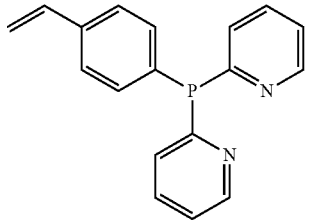
L-7

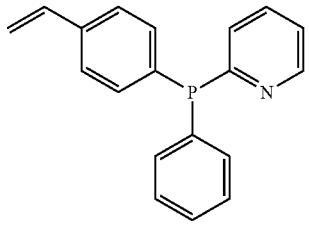
L-8

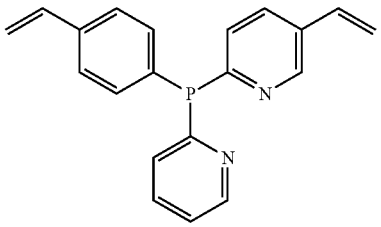
L-9

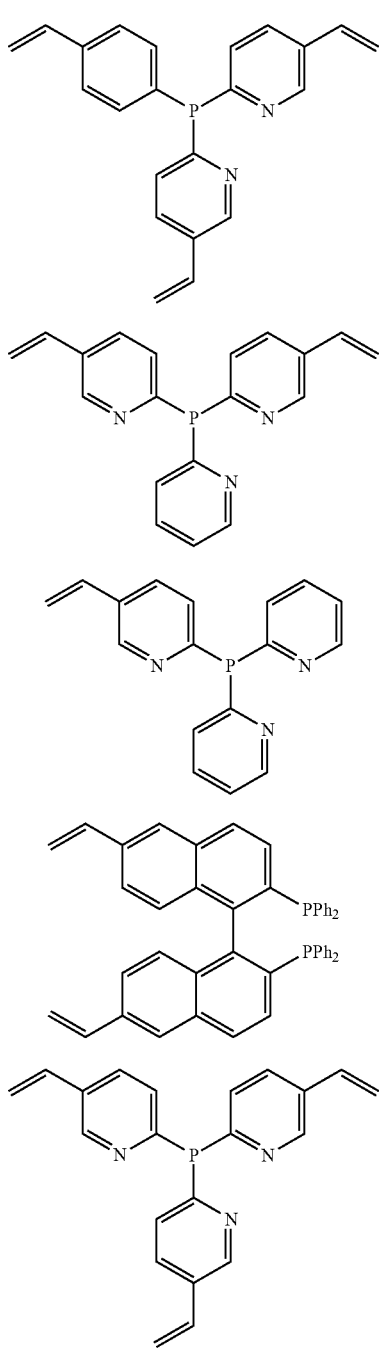

L-10

L-11

L-12

L-13

L-14

In order to describe the production method of the catalyst and the use thereof in the olefin hydroformylation reaction better, examples for the production of some catalyst samples (in which only tri(4-vinylphenyl)phosphine monomer (i.e. the monomer L-2 mentioned above) and di(4-vinylphenyl)-2-pyridylphosphine (i.e. the monomer L-6 mentioned above) are used as the exemplary organic ligand monomers for explanation) and use thereof in reaction process are provided below. However, the invention is not limited to the Examples listed. Unless otherwise indicated, the "percent" used in this application is by weight.

In the following Examples, all raw materials are as follows.

$H_2/CO$ mixed gas (containing 50 vol. % $H_2$ and 50 vol. % CO): Zhonghao Guangming Chemical Industry Research & Design Institute Ltd.

ethylene: Zhonghao Guangming Chemical Industry Research & Design Institute Ltd., purity≥99.999 vol. % tri(4-vinylphenyl)phosphine: synthesized by Zhejiang University, chemical pure di(4-vinylphenyl)-2-pyridylphosphine monomer: synthesized by Zhejiang University, chemical pure The measurement for the specific surface area and the pore size distribution of samples was performed on an Autosorb-1 adsorption analyzer of Quantachrome Instruments Co. Before test, the samples were pretreated at 373 K for 20 hours. A $N_2$ adsorption-desorption test was carried out at a liquid nitrogen temperature of 77 K.

Example 1

Production of an Organic Ligand Polymer 10.0 g tri(4-vinylphenyl)phosphine was dissolved in 100.0 ml tetrahydrofuran at 298 K under a protective atmosphere of nitrogen gas. 1.0 g radical initiator azodiisobutyronitrile was added into the above solution, and stirred for 2 hours. The stirred solution was kept standing at 373 K under a protective atmosphere of nitrogen gas for 24 h. Then it was cooled to room temperature, the solvent was drawn off at room temperature (about 298 K) under vacuum, and thereby a P-containing ligand polymer with hierarchical porosity was formed by polymerization from tri(4-vinylphenyl)phosphine via a solvothermal method. The technical route for the polymerization of the tri(4-vinylphenyl)phosphine ligand polymer support in this example was shown as follows:

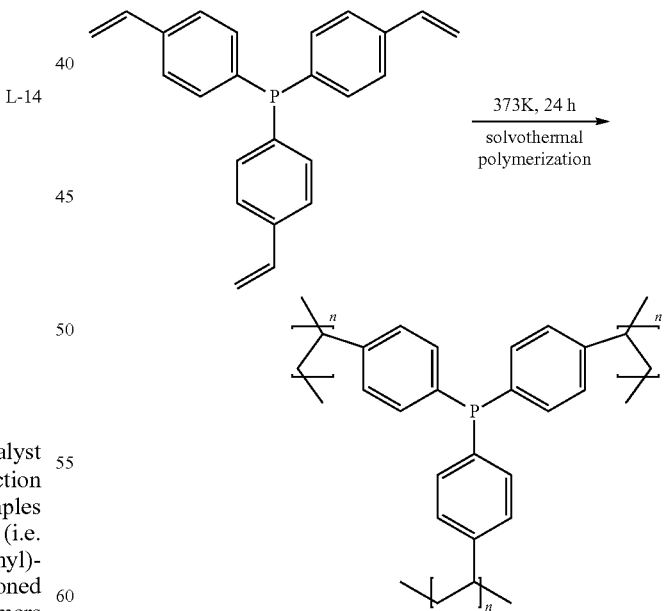

wherein the polymerization degree n was 450-550, the hierarchical porosity comprising macropores, mesopores, and micropores was contained, the BET specific surface area measured was 981 $m^2/g$, the pore volume was 1.45 $cm^3/g$, and the pore size distribution was 0.5 to 100.0 nm.

Example 2

Production of an Organic Ligand Polymer

The production procedure was same as in Example 1, except that the monomer di(4-vinylphenyl)-2-pyridylphosphine is used instead of the monomer tri(4-vinylphenyl)phosphine.

Example 3

Production of a Solid Heterogeneous Catalyst Containing 2 wt % Rh 50.10 mg of dicarbonylacetylacetonato rhodium (I) was added into a three-necked flask charged with 100.0 ml of tetrahydrofuran at 298 K under a protective atmosphere of nitrogen gas, stirred, and dissolved. 1.0 g of the P-containing ligand polymer with hierarchical porosity of Example 1 was added thereto. This mixture was stirred at 298 K under a protective atmosphere of nitrogen gas for 24 hours, then the solvent was drawn off at room temperature under vacuum, and thereby a solid heterogeneous catalyst, which has a metal Rh supported by the P-containing ligand polymer with hierarchical porosity itself, was obtained. The solid heterogeneous catalyst prepared above, which has an metal component supported by the tri(4-vinylphenyl)phosphine ligand polymer itself and hierarchical porosity, was charged into a fixed bed reactor. Ethylene gas as olefins and $CO/H_2$ mixed gas (in which the volume ratio of $H_2:CO=1:1$) in molar ratio of 1:2 were charged thereto. The reaction was started under the following conditions: at 393K, under 1.0 MPa, at a volume space velocity of the olefin gas of 1000 $h^{-1}$, at a volume space velocity of the $CO/H_2$ mixed gas of 2000 $h^{-1}$. The resultant liquid product propylaldehyde was collected in a cold trap collecting tank. The liquid product was analyzed by an HP-7890N gas chromatograph equipped with an HP-5 capillary column and a FID detector, using ethanol as the internal standard. The tail gas of the reaction was on-line analyzed by a HP-7890N gas chromatograph equipped with a Porapak-QS column and a TCD detector. The results of the reaction were shown in Table 1.

Example 4

Production of a Solid Heterogeneous Catalyst Containing 2 wt % Rh

In Example 4, the production steps and the conditions of the hydroformylation reaction were same as those in Example 3, except taking 0.5 mg of dicarbonylacetylacetonato rhodium (I) instead of 50.10 mg of dicarbonylacetylacetonato rhodium (I), which was dissolved in 100.0 ml of tetrahydrofuran. The results of the reaction were listed in Table 1.

Example 5

Production of a Solid Heterogeneous Catalyst Containing 10 wt % Co

In Example 5, the production steps for the catalyst and the conditions of the hydroformylation reaction are same as those in Example 3, except taking 398.25 mg of cobalt chloride instead of 50.10 mg of dicarbonylacetylacetonato rhodium (I). The results of the reaction were listed in Table 1.

Example 6

Production of a Solid Heterogeneous Catalyst Containing 0.4 wt % Rh-5 wt % Co In Example 6, the production steps for the catalyst and the conditions of the hydroformylation reaction were the same as those in Example 3, except taking 10.40 mg of dicarbonylacetylacetonato rhodium (I) and 199.13 mg of cobalt chloride instead of 50.10 mg of dicarbonylacetylacetonato rhodium (I). The results of the reaction were listed in Table 1.

Example 7

Production of a Solid Heterogeneous Catalyst Containing 0.125 wt % Rh

In Example 7, the production steps for the catalyst and the conditions of the hydroformylation reaction were same as those in Example 3, except weighing 3.13 mg of dicarbonylacetylacetonato rhodium (I) instead of 50.10 mg of dicarbonylacetylacetonato rhodium (I). The reaction was carried out continuously. The results of the reaction, which was carried out for 432 h, were listed in Table 1.

Example 8

Reaction Stability of the Catalyst Containing 0.125 wt % Rh

In Example 8, the production steps for the catalyst and the conditions of the hydroformylation reaction were same as those in Example 7. The reaction was carried out continuously. The results of the reaction, which was carried out for 1008 h, were listed in Table 1.

Comparative Example 1

Production of the Catalyst Containing 2 wt % Rh

In Comparative Example 1, the production steps for the catalyst and the conditions of the hydroformylation reaction were same as those in Example 3, except taking 1.0 g of $SiO_2$ instead of the organic ligand polymer formed by polymerizing tri(4-vinylphenyl)phosphine produced in Example 1. The results of the reaction were listed in Table 1.

TABLE 1 the ethylene hydroformylation reaction properties of the novel heterogeneous catalyst

| Example | Ethylene conversion, (%) | Selectivity (wt %) ethane | Selectivity (wt %) propylaldehyde |
| --- | --- | --- | --- |
| Example 3 | 98.0 | 3.5 | 96.5 |
| Example 4 | 42.3 | 0.9 | 99.1 |
| Example 5 | 15.1 | 4.9 | 95.1 |
| Example 6 | 89.5 | 2.9 | 97.1 |
| Example 7 | 96.9 | 5.1 | 94.9 |
| Example 8 | 97.1 | 5.2 | 94.8 |
| Comparative Example 1 | 38.9 | 0.8 | 99.2 |

Figure 2:
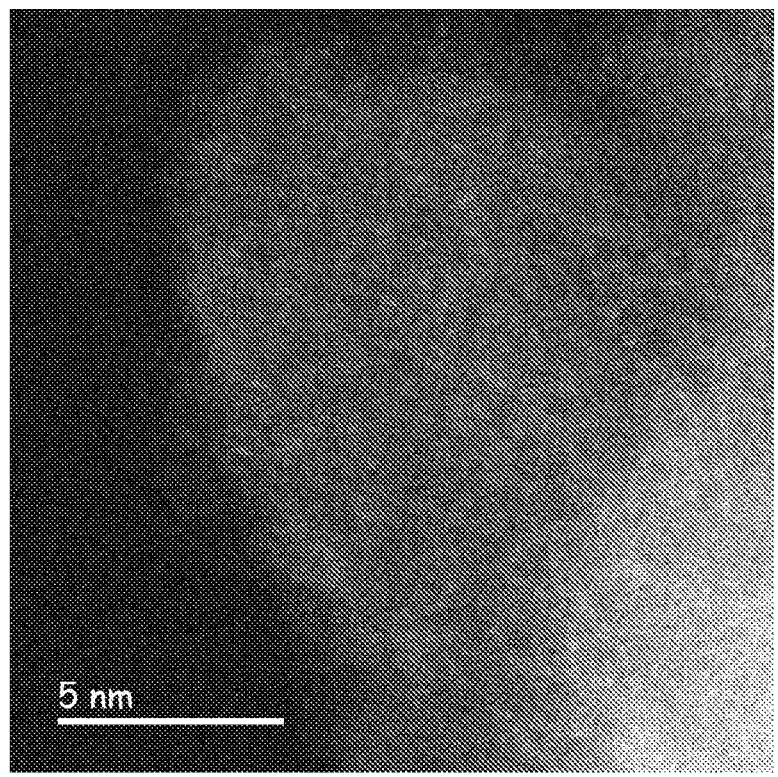
FIG. 2 is an HRTEM image of a catalyst sample after reacting continuously in ethylene hydroformylation for more than 1000 h according to a catalyst of the invention.

As can be known from the above-mentioned results, the heterogeneous catalyst containing an insoluble ligand of the invention, such as the polymer formed by self-polymerization of tri(4-vinylphenyl)phosphine, has an excellent catalytic activity and the catalyst can be easily separated, when it is used in the ethylene hydroformylation reaction in a fixed bed reactor. Meanwhile, as found by comparing Example 7 with Example 8, the catalyst has a very good stability. FIG. 1 shows that this kind of catalyst always has a stable activity during the long reaction process. At the same time, FIG. 2 shows that the active component Rh still remains in the monoatomic dispersion state on the surface of the polymer formed by polymerizing tri(4-vinylphenyl)phosphine, after a reaction lasting more than 1000 h.

The invention has been described in details above, but it is not limited to the particular embodiments described herein. Those skilled in the art will understand that other modifications and variations may be made, without departing the scope of the invention. The scope of the invention is defined by the appended claims.

The invention claimed is:

1. A solid heterogeneous catalyst for olefin hydroformylation reaction, wherein the solid heterogeneous catalyst consists of a metal component and an organic ligand polymer, wherein the metal component is one or more of Rh, Ir or Co, the organic ligand polymer is a polymer having a large specific surface area and hierarchical porosity formed by polymerizing an organic ligand monomer containing P and alkenyl group and optional N via a solvothermal polymerization process, the metal component forms coordinated bonds with the P atom or N in backbone of the organic ligand polymer and exists in a monoatomic dispersion state.

2. The solid heterogeneous catalyst according to claim 1, wherein the metal component accounts for 0.005 to 5.0% based on the total weight of the solid heterogeneous catalyst.

3. The solid heterogeneous catalyst according to claim 1, wherein the organic ligand monomer is an organic phosphine ligand monomer containing P and vinyl group and optional N.

4. The solid heterogeneous catalyst according to claim 1, wherein the organic ligand polymer has a specific surface area of 100 to 3000 $m^2/g$, a pore volume of 0.1 to 5.0 $cm^3/g$, and a pore size distribution of 0.2 to 50.0 nm.

5. A method for producing the solid heterogeneous catalyst of claim 1, comprising:

a) adding a radical initiator into an organic solvent containing an organic ligand monomer in an autoclave for synthesis at 273 to 473 K and under the protection of inert gas, and stirring it for 0.5 to 100 h;

b) keeping the solution of step a) in an autoclave for synthesis for 0.5 to 100 h at 273 to 473 K and under the protection of inert gas to perform a solvothermal polymerization reaction;

c) drawing off the solvent under vacuum at room temperature after the completion of step b), thereby obtaining the organic ligand polymer;

d) placing the organic ligand polymer in an organic solvent containing an active metal component, stirring it at 273 to 473 K and under the protection of inert gas for 0.5 to 100 h, and then drawing off the solvent under vacuum at room temperature, thereby obtaining the solid heterogeneous catalyst, in which the metal component is supported by the organic ligand polymer itself.

6. The method according to claim 5, wherein the organic solvent used in steps a) and d) is one or more of benzene, toluene, tetrahydrofuran, methanol, ethanol, or trichloromethane; the radical initiator used in step a) is one or more of cyclohexanone peroxide, dibenzoyl peroxide, tert-butyl hydroperoxide, azodiisobutyronitrile, or azodiisoheptonitrile.

7. The method according to claim 6, wherein the organic ligand monomer is an organic phosphine ligand monomer containing vinyl, and the organic solvent is benzene, toluene, or tetrahydrofuran.

8. The method according to claim 5, wherein the weight ratio of the radical initiator to the organic ligand monomer is 1:500 to 1:5.

9. An olefin hydroformylation method comprising conducting an olefin hydroformylation reaction in the presence of the solid heterogeneous catalyst according to claim 1, olefins, and $CO/H_2$ mixed gas in a fixed bed, a trickle bed, a slurry bed, or an autoclave reactor, at a reaction temperature of 323 to 573K, a reaction pressure of 0.05 to 20.0 MPa, and a volume space velocity of the gas of 100 to 20000 $h^{-1}$.

* * * * *